United States Patent [19]
Hamburger et al.

[11] Patent Number: 5,646,597
[45] Date of Patent: Jul. 8, 1997

[54] ALLERGEN DETECTOR SYSTEM AND METHOD

[75] Inventors: Robert N. Hamburger, 9485 La Jolla Shores Dr., La Jolla, Calif. 92037; Ruibo Wang; Jien-Ping Jiang, both of Tucson, Ariz.

[73] Assignee: Robert N. Hamburger, La Jolla, Calif.

[21] Appl. No.: 679,706

[22] Filed: Jul. 11, 1996

[51] Int. Cl.$^6$ ................................................. G08B 21/00
[52] U.S. Cl. ........................... 340/627; 340/630; 250/564; 250/574; 356/438; 116/214
[58] Field of Search ..................... 340/627, 630; 250/564, 565, 573, 574; 356/337, 339, 439, 438; 73/28.01, 28.04, 863.21–863.24; 116/214

[56] References Cited

U.S. PATENT DOCUMENTS

| | | | |
|---|---|---|---|
| 4,175,865 | 11/1979 | Horvath et al. | 340/630 |
| 4,249,244 | 2/1981 | Shofner et al. | 250/573 |
| 4,420,256 | 12/1983 | Fladda et al. | 250/574 |
| 5,001,463 | 3/1991 | Hamburger | 340/627 |
| 5,305,072 | 4/1994 | Sawada et al. | 356/336 |
| 5,383,024 | 1/1995 | Maxey et al. | 356/336 |
| 5,416,580 | 5/1995 | Trainer | 356/336 |
| 5,426,501 | 6/1995 | Hokanson et al. | 356/335 |

*Primary Examiner*—Jeffery Hofsass
*Assistant Examiner*—Daniel J. Wu
*Attorney, Agent, or Firm*—Brown, Martin, Haller & McClain

[57] ABSTRACT

An allergen particle detecting apparatus has a passageway through which environmental air is directed. A light beam is directed across the passageway so that portions of the beam will be scattered if any particles are present in the path of the beam. A beam blocking device on the opposite side of the passageway blocks any non-scattered portion of the beam while transmitting any scattered portions of the beam along a light path in the apparatus. Any light scattered by allergen size particles will be traveling in a predetermined angular range, and a pinhole device is positioned in the light path so as to transmit only light traveling in that angular range. Light transmitted through the pinhole device is detected by a light detector and an alarm output signal is produced if the detected amount of light is above a predetermined level.

19 Claims, 3 Drawing Sheets

1

ALLERGEN DETECTOR SYSTEM AND METHOD

BACKGROUND OF THE INVENTION

The present invention is directed to a system and method for detecting airborne allergen particles and for providing an alarm or operating a filtering system if the detected amount of allergen particles is above a predetermined level.

Many individuals suffer from allergies to airborne particles such as dust, pollen and the like which are often present in the environmental air breathed by the individual. The particulates to which many individuals are sensitive are typically in the 5 to 50 micron range. The presence of such particles in air breathed by sensitive or allergic individuals may give rise to symptoms such as asthma, coughing, sneezing, as well as skin rashes and anaphylaxis. Knowledge or warning of the presence of high levels of allergenic particles in the environmental air is helpful to such individuals, potentially enabling them to take medication, leave the area, or activate allergen removing filters, before the onset of serious symptoms.

In U.S. Pat. No. 5,001,463 of Hamburger an allergen particulate detecting apparatus is described in which air is blown through a passageway in which an allergen particle sensor is mounted for trapping allergen-sized particles. The output signal of the sensor is dependent on the amount of trapped particles, and an alarm is activated if the signal is above a predetermined level.

SUMMARY OF THE INVENTION

It is an object of the present invention to provide a new and improved allergen detection system and method.

According to one aspect of the present invention, an allergen particle detection system is provided which comprises an outer housing having a passageway for air flow through the housing, a light source on one side of the passageway for directing a light beam through the air flowing through the passageway, a beam blocking device on the other side of the passageway for blocking the direct light beam from the light source and transmitting any light scattered by impact with particles in the light path through the passageway, a pinhole positioned in the path of light transmitted through the beam blocking device for blocking passage of light outside a predetermined range of scattering angle corresponding to a predetermined particle size range, a detector positioned to receive light transmitted through the pinhole, and a control circuit connected to the detector for generating an alarm output signal if the detector output is above a predetermined level.

The alarm output signal may be used to activate an audible or visual alarm device, or to turn on a filtration and ventilation system including HEPA or allergen particle filters. The filtration system may be turned off as soon as the detected allergen particles have returned to a safe level. The apparatus may be relatively small, and may be conveniently designed for wall mounting.

According to another aspect of the present invention, a method of detecting allergen particles in the air is provided which comprises the steps of directing air flow along a passageway, directing a light beam across the path of the air flowing through the passageway so that light will be scattered by any particles in the air, blocking the direct light beam on the opposite side of the passageway and transmitting any light which has been scattered by impact with particles along a light path, positioning a pinhole at a predetermined position in the light path and transmitting only light within a predetermined range of scattering angle through the pinhole, detecting light transmitted through the pinhole and producing a first output signal at a level proportional to the amount of light transmitted, and generating an alarm output signal if the first output signal is above a predetermined level.

This system and method readily discriminates between allergen size particles in the 5 to 50 micron range and larger, non-allergenic particles so as to produce an accurate indication of the allergen particle levels in a room or enclosed area. Preferably, the level at which the alarm signal is produced is adjustable. The apparatus can be readily connected to turn on auxiliary air cleaning appliances or filters such as HEPA filters.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENT

Figure 1:
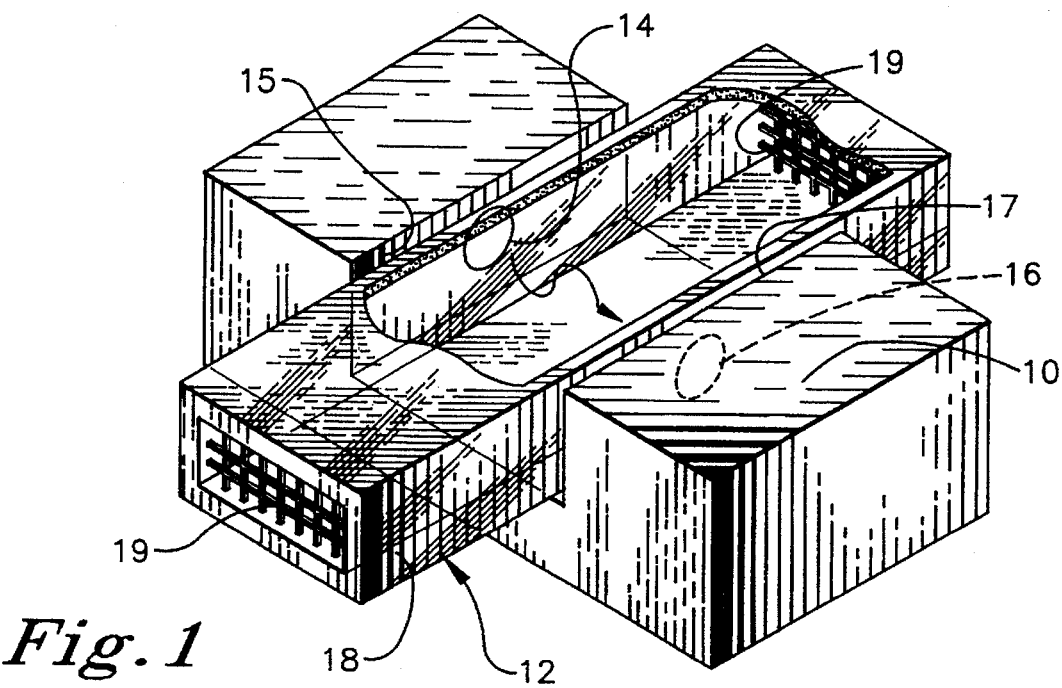
FIG. 1 is a perspective view of an allergen particle detector apparatus according to a preferred embodiment of the present invention.
Figure 2:
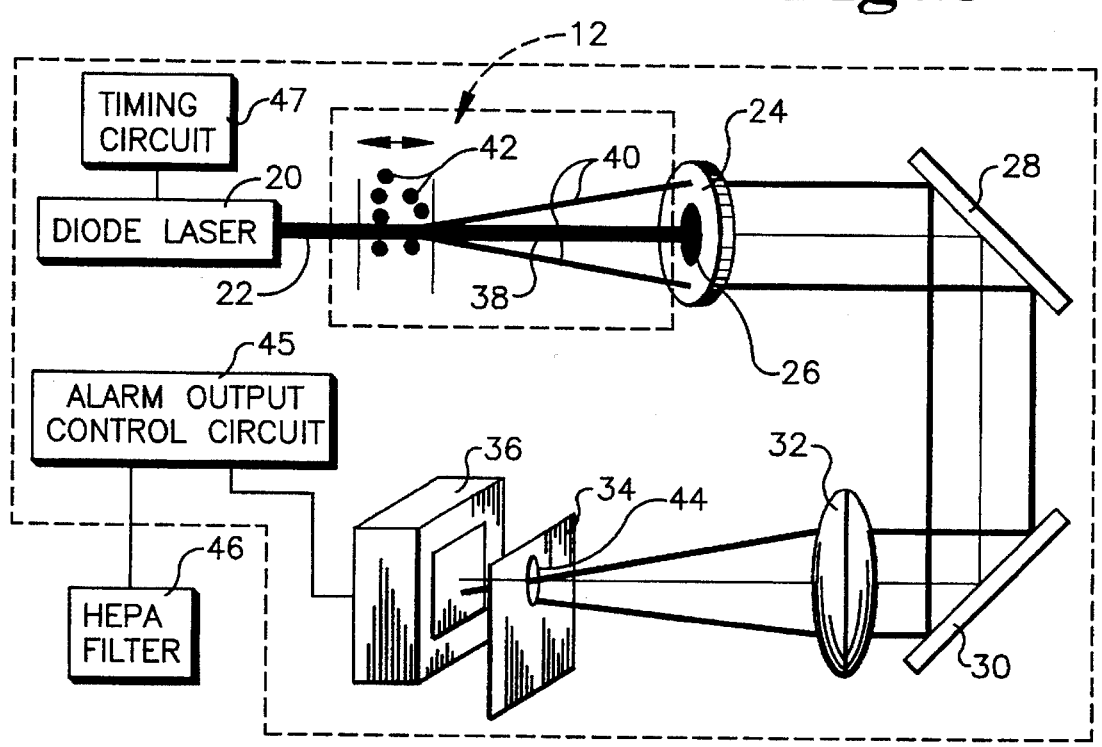
FIG. 2 is a schematic block diagram of the optical system.
Figure 3:
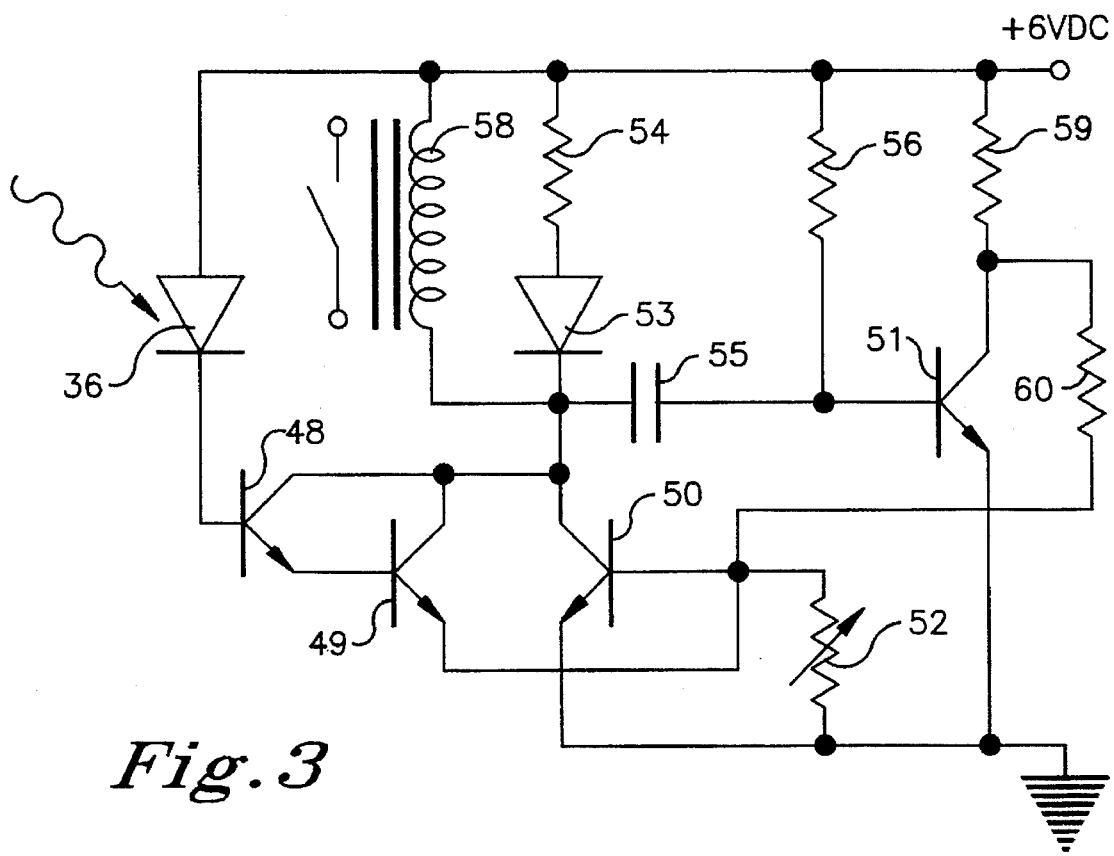
FIG. 3 is a circuit diagram of the electrical control circuit.
Figure 4:
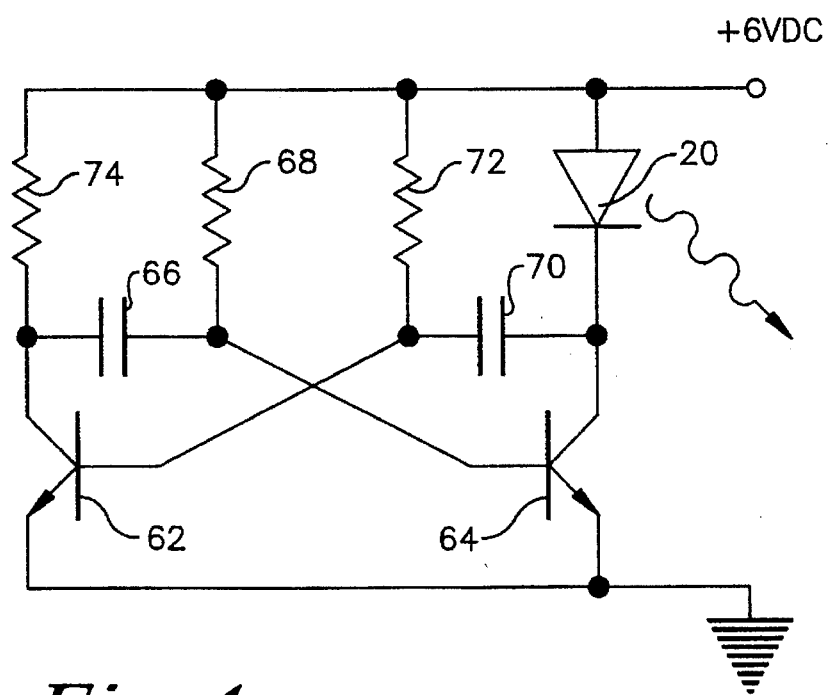
FIG. 4 is a diagram of the timing circuitry.
Figure 5:
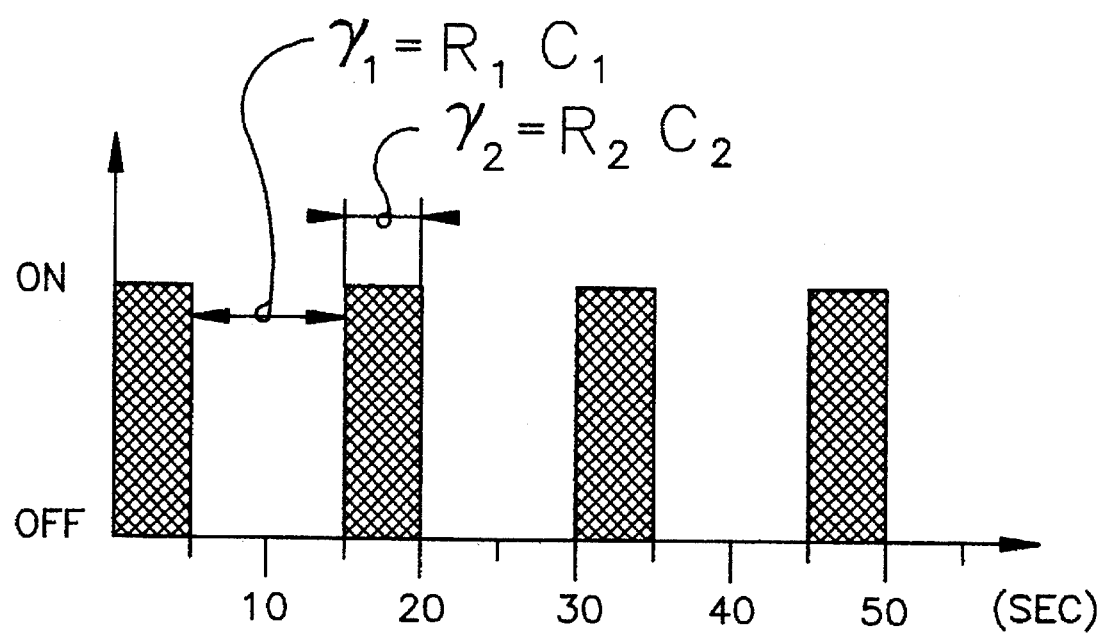
FIG. 5 is a timing diagram.

FIGS. 1 and 2 of the drawings illustrate an allergen particle detector apparatus according to a preferred embodiment of the present invention, while FIGS. 3–5 illustrate details of the electrical control circuitry. The apparatus basically comprises an outer housing 10 shaped to provide a passageway 12 across which a laser beam is directed from laser diode 20 through opening 14 in one side wall 15 of the passageway into opening 16 on the opposite side wall 17 of the passageway. A rectangular, transparent plastic tube 18 is releasably mounted in the passageway. Tube 18 is open at opposite ends, and a grating or grille 19 is preferably mounted in each open end to prevent access to the interior of the tube. Tube 18 permits air flow through the passageway and through the path of the laser beam 22 directed across the passageway.

As best illustrated in FIG. 2, a beam blocking device 24 is mounted in the opening 16 facing the laser beam. The device 24 comprises a transparent circular flat glass plate with an opaque portion 26 at the center of the plate. Portion 26 may be produced by black paint, or a black plastic or metal insert at the center of the plate. The actual dimensions of the opaque blocking portion will be dependent on the cross-sectional shape and dimensions of the output beam of laser diode 20. The laser diode may emit infrared light (0.8–1.0 micron), but in one embodiment of the invention a laser diode emitting at the wavelength of 670 nm. was used. This device has an output beam of elliptical shape, with a long axis of 3 mm and a short axis of 2 mm. The blocking portion 26 in this example will therefore also be of elliptical shape and slightly larger dimensions than the laser diode output beam, to ensure all direct light is blocked.

An extended light path or passageway is defined in the housing from blocking device 24. A first mirror 28 is positioned in the light path from device 24 for redirecting light in a first direction, and a second mirror 30 is positioned to intercept light reflected from mirror 28 and direct it back in the opposite direction via a lens 32 and a pinhole device 34 to a photodetector 36. The output of photodetector 36 is connected to electronics and timing circuitry which is described in more detail below in connection with FIGS. 3–5.

A portion 38 of the laser light beam directed across the passageway will pass straight to the blocking device 24 without scattering, while other portions 40 of the beam will encounter particles 42 and will be scattered at angles dependent on the particle size. The opaque central portion 26 of the blocking device is designed to block transmission of the unscattered portion 38 of the light beam, while all scattered portions will be transmitted through the transparent peripheral portion of the device. Scattered portions of the beam will be reflected by mirrors 28,30 towards pinhole device 34. The pinhole device 34 comprises an opaque plate with a pinhole 44 at a predetermined position such that only light scattered in a predetermined angular range will pass through the pinhole.

The output of photodetector 36 is connected to an alarm output control circuit 45 which is illustrated in more detail in FIG. 3. The circuit 45 preferably has a suitable output for connection to an allergen filter device such as a HEPA filter 46, or an alarm device or the like. An audible alarm device or an alarm light emitting diode (LED) may be mounted within the housing. A timing circuit 47, illustrated in more detail in FIGS. 5 and 6, controls operation of the laser diode 20.

Airborne particles are typically present in the air in a large range of sizes. Allergen particles such as pollen, dust, mold spores and the like are in the size range from 5 to 50 microns. Larger particles typically cannot pass through the nose and do not normally cause any problem. The optical system as illustrated in FIG. 2 is designed to discriminate between light scattered by particles in the allergen size range and light scattered by larger particles. Airborne particles of different sizes have quite different light scattering properties. Only particles with sizes comparable to the wavelength of the incident light will have well pronounced scattering maxima in the forward direction of light propagation. Allergen particles have sizes ranging from 2 to 10 times the incident light wavelength, and for these sizes the maximum scattering angle will be in the range from 30° to 40°. The pinhole 44 is placed at an off-axis position which corresponds to an angular direction in the 30° to 40° range. The exact off-axis distance, h, can be calculated according to the following relationship:

$$h = \left[ (l_o + l_p) - \frac{l_o \cdot l_p}{f} \right] \tan\theta \quad 1$$

where $\theta$ is the scattering maximum angle, $l_o$ is the distance of the scattering particles from the lens, f is the focal length of the lens, and $l_p$ is the distance of the screen with the pinhole from the lens.

With the pinhole placed at the calculated position, only light scattered by particles in the allergen particle size range will be transmitted through the pinhole and detected by the photodetector. FIG. 3 illustrates the circuit for receiving the photodetector output and producing an alarm output signal if the output is above a predetermined level. FIGS. 4 and 5 illustrate timer circuitry for controlling the laser diode.

Referring first to FIG. 3, the output of photodiode or photodetector 36 is amplified by transistors 48,49. Transistors 50,51 act as level discriminators for determining when the output of the photodetector is above a preset level. The amplified output is connected to the base of transistor 50. Depending on the setting of a variable resistor 52, the input current can turn on transistor 50 and an alarm LED 53 which is mounted on the front panel of the housing. The switching on of transistor 50 also turns on relay 58, acting to switch on suitable filtering devices such as a HEPA filter as indicated in FIG. 2. The alarm LED is connected in series with resistor 54 to the 6 volt DC power supply. The sensitivity of the device can be set by adjusting the resistor 52. After transistor 50 is turned on, capacitor 55 starts to charge through charging resistor 56 and, after a time period set by the time constant ($\tau = R \times C$), the charge accumulated on the capacitor will turn on transistor 51. This will pull the current at the base of transistor 50 to zero and turn it off, thus shutting off the LED and the relay. Resistor 59 is connected in parallel with transistor 51, and resistor 59 is connected in series with the transistor 51. The value of capacitor 55 and resistor 56 will therefore determine the length of time that the LED and relay are on. The relay may be used to control a filtration and ventilation system or any device to filter out the allergen particles from the environmental air.

The timer circuit of FIG. 4 is used to control the laser diode 20 to turn on and off periodically, in order to lower the power consumption. Timing is provided by a bistable resistor circuit as illustrated in FIG. 4. When the power supply is turned on, current will flow to one of the two transistors 62,64, for example transistor 62. After transistor 62 is turned on, the capacitor 66 begins to be charged up through resistor 68. In this period there is no current flowing through the laser diode and the device is in the "OFF" mode. After a time period $\tau_1 = R_1 \times C_1$, the charges accumulated on capacitor 66 are sufficient to turn on the transistor 64, and this allows current to flow through the laser diode, switching the diode to the "ON" mode. At the same time, capacitor 70 will be charged up through resistor 72, and after a time period $\tau_2 = R_2 \times C_2$, the accumulated charges will turn on transistor 62 again, turning off the laser diode. This completes the cycle. The duty cycle of the timer circuit can be controlled by setting the values of capacitors 66 and 70 and resistors 68 and 72, as indicated in FIG. 5.

The housing is appropriately mounted in a room or other enclosed area where the level of allergen particulates is to be monitored. It may be designed for wall mounting so that only the air sampling area in passageway 12 is exposed. Environmental air will flow through tube 18 into the sampling area between the laser diode and the beam blocking device. If the air is free from any particulates, there will be no scattered light and the entire laser beam will be blocked by the central blocking region of the blocking device 24. Thus, no alarm signal will be generated. When there are airborne particulates 42 present, some of the laser beam will be scattered by those particles, and the scattered light will deviate from the original light path and will not be blocked by the blocking device 24. The amount of scattered light will be proportional to the number of particles 42 present.

All particles present in the air, including allergen particles, will cause scattering of the light, and the scattered light will travel along the light path and be reflected by mirrors 28 and 30 towards the lens 32 and pinhole device 34, which together form a discriminator to discriminate between allergen size particles and particles of other sizes. As explained in detail above, the pinhole 44 is placed such that only light scattered in a specific scattering angle range will pass through the pinhole, with light scattered in other directions being blocked. Thus, only light scattered by allergen-size particles passes through the pinhole and is detected by photodetector 36. If the amount of light detected is above a threshold set by adjustable resistor 52, the alarm LED 53 will be turned on and the relay 58 is actuated to turn on an allergen filtering device such as a HEPA filter, or a room air conditioning unit including a filtering device. Additionally, an audible alarm may be actuated. Preferably, an adjustment dial is provided on the housing to enable the user to adjust the resistance of resistor 52, and thus vary the sensitivity of the device. The device turns off when the detected allergen levels fall below the selected threshold value. A digital counter may be included to record the number of occurrences of allergen detection in a given period of time.

The two mirrors allow the light path within the housing to be extended, improving sensitivity. A system of more sensitivity may be provided by directing the light beam around the periphery of a room with appropriately positioned mirrors.

If desired, a timer circuit may be added to the system. This will provide a suitable alarm signal if the air is not cleaned within a certain time period after the filter unit is turned on, indicating a potential failure of the room filtering system. The control circuit of FIG. 3 may be a hard-wired device as illustrated or may alternatively be made as a printed circuit board in a simplified structure. This will take up less space within the housing and will reduce the problem of cross-talk between the electrical components. The entire device may be run from a single rechargeable 9-volt battery or other batteries, or may be connectable to a main power supply.

This apparatus enables up to 99% of airborne allergen particles to be detected, while larger, non-allergenic particles are not detected. For the safety of users, the clear plastic tube 18 is mounted in the air passageway 12 in the housing. The tube 18 is designed to be readily removable at periodic intervals when build up of dust on the internal surfaces of the tube causes a problem. At this point, it can be slid out of the passageway for cleaning or replacement with a new tube. The tube will prevent insertion of fingers or mirrors into the laser beam, making the device essentially child-proof. The rectangular design of the tube avoids unwanted distortion of the laser beam passing through the transparent side walls of the tube.

The laser pulse period may be set by the user as desired, to periods of 1 second, 1 minute, 10 minutes, 20 minutes, and so on, using an appropriate setting dial provided on an outer face of the housing. If the laser pulse length is set to be 10 seconds, then the setting dial will have sampling settings of continuous (the 1 second off setting is equivalent to continuous operation), 10 minutes per hour, 1 minute per hour, 30 seconds per hour, and so on.

The allergen particle detector of this invention has the advantage that only allergen-size particles are detected, due to the design of the optical system for eliminating light scattered by particles of sizes outside the allergen size range of 5 to 50 microns. The allergen detection level may be readily adjusted by the user. The apparatus is easy and inexpensive to manufacture, and simple to operate. It provides real time, accurate detection of excessive levels of allergen particles in the air, providing a warning to sensitive individuals who may need medication and also allowing allergen filtering equipment to be activated under such conditions to clean the air.

Although a preferred embodiment of the present invention has been described above by way of example only, it will be understood by those skilled in the field that modifications may be made to the disclosed embodiment without departing from the scope of the invention, which is defined by the appended claims.

We claim:

1. An allergen detecting apparatus for detecting the presence of allergen particles in environmental air, comprising:
   an outer housing having a passageway for air flow through the housing;
   a light source on one side of the passageway for directing a light beam through the air passing through the passageway;
   a beam blocking device on the other side of the passageway facing the light source for blocking any portion of the light beam transmitted directly across the passageway without scattering and transmitting any portion of the light beam scattered by impact with particles in the light path;
   a light passageway in the housing extending from the beam blocking device for directing light transmitted through the beam blocking device along a light path;
   a discriminating device positioned in the light path for transmitting light traveling in a predetermined scattering angle range and blocking transmission of light scattered outside said scattering angle range;
   a detector positioned in the light path after the discriminating device for detecting light transmitted through the discriminating device and producing an output signal proportional to the amount of light transmitted; and
   a control circuit connected to the detector output for generating an alarm output signal if the detector output is above a predetermined level.

2. The apparatus as claimed in claim 1, including an alarm indicating device connected to said control circuit and responsive to said alarm output signal and having an alarm condition indicator which is actuated by said alarm output signal.

3. The apparatus as claimed in claim 2, wherein said alarm indicating device is a light emitting diode.

4. The apparatus as claimed in claim 1, including a HEPA filter connected to said control circuit and having a switch for switching on the HEPA filter in response to said alarm output signal.

5. The apparatus as claimed in claim 1, wherein said discriminating device comprises a lens and a pinhole device positioned in series in the light path, the pinhole device having a pinhole at a predetermined position for transmitting light traveling in a predetermined angular path after the lens.

6. The apparatus as claimed in claim 5, wherein the pinhole is positioned for transmitting light scattered by particles in a 5 to 50 micron size range.

7. The apparatus as claimed in claim 1, including first and second mirrors in the light path between the blocking device and the discriminating device for reflecting light traveling on the light path through 180°.

8. The apparatus as claimed in claim 1, including a transparent plastic tube removably mounted in the passageway, the tube having opposite, open ends for air flow through the tube.

9. The apparatus as claimed in claim 8, including a grating mounted over each open end of the tube.

10. The apparatus as claimed in claim 1, wherein the light source is a laser diode.

11. The apparatus as claimed in claim 10, including a timing circuit connected to the laser diode to control the diode to pulse on and off at predetermined time intervals.

12. The apparatus as claimed in claim 1, including an adjustment device for adjusting said predetermined level.

13. The apparatus as claimed in claim 12, wherein the adjustment device comprises a variable resistor.

14. The apparatus as claimed in claim 12, wherein the adjustment device includes a digital counter to record the number of occurrences of allergen detection in a given duration of time.

15. A method of detecting the quantity of allergen particles in the air, comprising the steps of:

directing environmental air to flow along a passageway;

directing a light beam from one side of the passageway transversely through the air flowing along the passageway, whereby a portion of the light beam will be scattered by any particles present in the path of the light beam;

blocking the direct light beam on the opposite side of the passageway and transmitting any scattered portion of the light beam along a light path;

blocking scattered portions of the light beam traveling in directions outside a predetermined angular range corresponding to a predetermined particle size range with a discriminating device in the light path and transmitting any part of the scattered light beam travelling within said predetermined angular range;

detecting the amount of light transmitted through the discriminating device; and producing an output alarm signal if the amount of light detected is above a predetermined level.

16. The method as claimed in claim 15, wherein the step of blocking scattered portions of the light beam outside the predetermined angular range comprises placing a light blocking plate in the light path with a pinhole at a predetermined position for transmitting light traveling in the predetermined angular range.

17. The method as claimed in claim 16, wherein the predetermined angular range is 30° to 40°.

18. The method as claimed in claim 15, including the step of using the output alarm signal to activate an allergen filtering device.

19. The method as claimed in claim 18, including the step of switching off the allergen filtering device when the light detected falls below the predetermined level.

* * * * *